United States Patent [19]
König

[11] 3,948,794
[45] Apr. 6, 1976

[54] ADHESIVE COMPOSITIONS CONTAINING A CYANOACRYLATE AND ITACONIC ANHYDRIDE

[75] Inventor: Eberhard König, Eschborn, Germany

[73] Assignee: USM Corporation, Boston, Mass.

[22] Filed: June 12, 1974

[21] Appl. No.: 478,514

[30] Foreign Application Priority Data
June 16, 1973 United Kingdom............ 28717/73

[52] U.S. Cl.......... 252/182; 260/78.5 R; 260/78.5 N
[51] Int. Cl.²....................................... C08F 222/32
[58] Field of Search............ 252/182, 407; 260/881, 260/78.4 N, 78.5 N, 78.5 R

[56] References Cited
UNITED STATES PATENTS

| | | |
|---|---|---|
| 2,765,332 | 10/1956 | Coover et al............. 260/78.4 N X |
| 2,873,211 | 2/1959 | Roeser........................... 260/78.5 N |
| 3,223,083 | 12/1965 | Cobey........................ 260/78.4 N X |
| 3,564,078 | 2/1971 | Wicker et al...................... 260/881 |
| 3,697,618 | 10/1972 | Grunewalder et al........ 260/78.5 R |
| 3,832,334 | 8/1974 | O'Sullivan...................... 260/78.5 R |

*Primary Examiner*—Benjamin R. Padgett
*Assistant Examiner*—David Leland
*Attorney, Agent, or Firm*—Benjamin C. Pollard; Vincent A. White; Richard B. Megley

[57] ABSTRACT

Adhesive compositions based on 2-cyanoacrylate monomers in which storage stability, cure speed and other properties are improved by inclusion of itaconic acid anhydride.

5 Claims, No Drawings

ADHESIVE COMPOSITIONS CONTAINING A CYANOACRYLATE AND ITACONIC ANHYDRIDE

FIELD OF THE INVENTION

This invention is concerned with improvements in or relating to adhesive compositions and is especially concerned with adhesive compositions based on 2-cyanoacrylates.

BACKGROUND OF THE INVENTION

Adhesive compositions based on 2-cyanoacrylates may be used as single-part liquid adhesives for bonding a variety of materials. Examples of materials to which adhesive bonds can be formed by use of 2-cyanoacrylate adhesives include metals, plastics, glass and rubbers, and such materials are met with as parts of precision instruments and household articles. It has also been proposed to use cyanoacrylate based adhesives for bonding blood vessels, living tissue in surgical operations, and vegetable tissue in grafting.

Although adhesive compositions based on 2-cyanoacrylates are potentially suitable for use in a wide variety of applications, they tend to have various attendant problems including ones relating to storage stability, cure speed and bond performance.

When 2-cyanoacrylates are stored even in tightly closed vessels they exhibit a tendency to polymerize within a relatively short period of time at normal room temperatures. At higher temperatures this tendency to polymerize is enhanced. It has been proposed therefore to include in adhesive compositions based on 2-cyanoacrylates anionic polymerisation inhibitors, e.g., $P_2O_5$ or $SO_2$, in combination with a free radical polymerization inhibitor, e.g., hydroquinone or monomethyl ether of hydroquinone.

Compositions based on 2-cyanoacrylates containing anionic polymerization inhibitors and free radical polymerization inhibitors have not generally fully overcome difficulties associated with cure speed and bond performance. Cure speed difficulties in general appear to result from a lack of tackiness of the composition necessitating holding of parts to be bonded in appropriate correlation with the adhesive betweem them until the 2-cyanoacrylate polymerises, and builds up sufficient bonding strength. Bonds formed with 2-cyanoacrylates tend to be rather brittle, become unreliable when aged and tend not to resist strongly deterioration caused by heat.

SUMMARY OF THE INVENTION

It is an object of the present invention to provide a 2-cyanoacrylate adhesive composition including a novel agent effective to improve storage stability, cure speed and other properties of the composition.

This and other advantages are obtained according to the present invention by the inclusion in adhesive compositions based on 2-cyanoacrylate ester monomer of small amounts of itaconic acid anhydride.

DESCRIPTION OF THE PREFERRED EMBODIMENTS

The adhesive composition of the present invention is based on one or more esters of 2-cyanoacrylic acid according to the general formula.

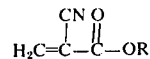

where R is an alkyl or alkenyl group having 1 to 16 carbon atoms, a cyclohexyl group or a phenyl group, together with an anionic polymerisation inhibitor and a free radical polymerisation inhibitor, characterized in that the adhesive includes an amount of itaconic acid anhydride.

In an adhesive composition according to the invention, the ester of 2-cyanoacrylic acid is preferably methyl-2-cyanoacrylate, ethyl-2-cyanoacrylate, allyl-2-cyanoacrylate or mixtures of these with each other. A proportion of allyl-2-cyanoacrylate may be found particularly appropriate where good resistance to deterioration of bonds by heat is desirable, for example a mixture comprising methyl-2-cyanoacrylate and about 2% by weight of the mixture of allyl-2-cyanoacrylate. Other examples of mixtures are those comprising methyl-2-cyanoacrylate and up to 50% by weight of the mixture of ethyl-2-cyanoacrylate or up to 50% by weight of the mixture of allyl-2-cyanoacrylate.

In an adhesive composition according to the invention, we believe that itaconic acid anhydride contributes towards storage stability of the 2-cyanoacrylates by virtue of its anhydride grouping, and to performance of adhesive bonds formed by use of 2-cyanoacrylate based adhesive compositions as a result of copolymerization with the 2-cyanoacrylate by virtue of its exocyclic ethylenic double bond. Suitably, from 0.1 to 10% by weight itaconic acid anhydride may be used by weight of the composition. The quantity of itaconic acid anhydride used is chosen in light of properties required of the adhesive including stability and cure time requirements, and it is noted that the most appropriate amount to be used is dependent to some extent on the type of 2-cyanoacrylate used at least so far as bond strength is concerned. With the preferred 2-cyanoacrylates excellent results appear to be obtainable by use of from about 0.5 to about 3% (by weight of the composition) of itaconic acid anhydride. It appears that the setting time of the composition (i.e., the time which elapses between pressing together brass sheets with a drop of the composition and the onset of immovability of the sheets with respect to each other) is not significantly adversely effected by the presence of such quantities of itaconic acid anhydride.

In an adhesive composition according to the invention stabilizing quantities of an anionic or acidic polymerisation inhibitor and a free radical inhibitor are used. The anionic polymerization inhibitor employed may be for example any one of those materials commonly known as acidic polymerization inhibitors for 2-cyanoacrylates, for example $P_2O_5$ or $SO_2$. Similarly the free radical polymerization inhibitor may be for example one of those materials commonly known as free radical polymerization inhibitors for 2-cyanoacrylates for example hydroquinone or monomethyl ether of hydroquinone. These materials may be used in appropriate quantities; for example in the preferred compositions quantities of the order of 0.01 to 0.02% (by weight of the composition) monomethyl ether of hydroquinone and 0.001% (by weight of the composition) $P_2O_5$ are used.

In an adhesive composition according to the invention there may be included materials intended to increase the viscosity of the fluid composition so that it is somewhat thickened and thereby may be more easily applied. A polymeric material may be used for this purpose, for example polymethyl methacrylate or a copolymer compound formed from 2-cyanoacrylate and styrene or methyl styrene as more fully described in the U.S. Patent application Ser. No. 490,044 in the names of Heinz Tomaschek and Victor Winkovic entitled "Improvements in or relating to Adhesive Compositions" filed July 19, 1974.

In order that the above and others of the various aspects of the invention may become more clear there are hereinafter described various examples of 2-cyanoacrylate based adhesive compositions of which 10 adhesive compositions are illustrative of aspects of the invention. It is of course to be clearly understood that the illustrative examples have been selected for description to illustrate the invention by way of example only and not by way of limitation thereof.

EXAMPLE 1

This example illustrates the extended storage stability of 2-cyanoacrylate adhesive compositions containing itaconic acid anhydride.

CONTROL COMPOSITION 1

This comprised methyl-2-cyanoacrylate stabilized with 0.01% by weight monomethyl ether of hydroquinone and 0.001% by weight phosphorus pentoxide. Control composition 1 polymerized after a storage period of 60 days at 45°C.

FIRST ILLUSTRATIVE COMPOSITION

This was formed by adding to a sample of Control Composition 1, an additional amount of itaconic acid anhydride to provide 1% by weight of the illustrative composition. It was observed that the composition remained fluid for 80 days at 45°C and increased in viscosity after this period, and remained fluid for 90 days at room temperature.

CONTROL COMPOSITION 2

This comprised ethyl-2-cyanoacrylate stabilized with 0.01% by weight monomethyl ether of hydroquinone and 0.001% by weight $P_2O_5$. This composition polymerized after a storage period of 60 days at room temperature.

SECOND ILLUSTRATIVE COMPOSITION

This was formed by adding to a sample of Control Composition 2 an additional amount of itaconic acid anhydride to provide 1% by weight of the adhesive composition. This composition remained fluid for 90 days at room temperature.

CONTROL COMPOSITION 3

This comprised a mixture of 98% by weight methyl-2-cyanoacrylate and 2% by weight allyl 2-cyanoacrylate stabilized with 0.01% by weight monomethyl ether of hydroquinone and 0.001% $P_2O_5$. This composition polymerized after 40 days storage at room temperature.

THIRD ILLUSTRATIVE COMPOSITION

This was formed by adding to a sample of Control Composition 3 sufficient itaconic acid anhydride to provide 1% by weight of the adhesive composition. This composition remained fluid for 90 days at room temperature.

EXAMPLE 2

This Example and Example 3 illustrate improved tensile shear strength of 2-cyanoacrylate adhesive compositions containing itaconic acid anhydride. One drop of control composition 1 was placed between overlapping portions of two brass sheets (dimensions 150 × 10 × 5 mm) which had been thoroughly cleaned with acetone before application of the composition. The bonds were formed by holding the sheets together, and were aged for 1 hour at room temperature and then were broken in tension on an Instron 1113/4 testing machine at a cross-head separation speed of 10 mm/min. A tensile shear strength of 160 $Kp/cm^2$ was obtained.

Using the first illustrative composition to form bonds as just above set out, and testing them in the same way after ageing them for 1 hour at room temperature, a tensile shear strength test result of 192 $Kp/cm^2$ was obtained.

EXAMPLE 3

CONTROL COMPOSITION 4

This comprised allyl-2-cyanoacrylate stabilized with 0.01% (by weight of the composition) monomethyl ether of hydroquinone and 0.001% (by weight of the composition) $P_2O_5$.

One drop of this composition was placed between two brass sheets (dimensions 150 × 10 × 5 mm) and a bond formed as described in Example 2. The tensile shear strength of the bonds, evaluated (after ageing for 1 hour at room temperature) as described in Example 2 was 55 $Kp/cm^2$.

FOURTH ILLUSTRATIVE COMPOSITION

This was formed by adding amount (to provide 1% by weight of the fourth illustrative composition) of itaconic acid anhydride to a sample of Control Composition 4. The tensile sheer strength of bonds formed by use of this fourth illustrative composition as set out in Example 2 and evaluated (after ageing for 1 hour at room temperature) as in Example 2, was observed to be 105 $Kp/cm^2$.

EXAMPLE 4

The tensile shear strength of bonds formed as described in Example 2 but using control Composition 3 or various illustrative compositions prepared from it by addition of various amounts of itaconic anhydride was measured (after ageing for 1 hour at room temperature) as in Example 2. The results are as shown:

| Composition | Control | Illustrative | | | |
| --- | --- | --- | --- | --- | --- |
| | 3 | 5th | 3rd | 6th | 7th |
| Amount of itaconic anhydride (% by weight of composition) | 0 | 0.5 | 1 | 1.5 | 2 |
| Tensile shear strength ($Kp/cm^2$) | 135 | 184 | 200 | 191 | 158 |

EXAMPLE 5

This Example illustrates the strength of bond to be achieved after a relatively short time by use, in Control composition 5, of itaconic acid anhydride.

Control composition 5 comprised 50% by weight allyl-2-cyanoacrylate and 49.9% methyl-2-cyanoacrylate stabilized as in Control Composition 1.

Eighth and ninth illustrative compositions were formed by addition of various amounts of itaconic acid anhydride to Control composition 5.

The tensile shear strength of bonds formed as described in Example 2 but using Control composition 5 or the eighth or ninth illustrative composition was measured. These bonds were allowed to cure for 2 minutes only at room temperature before being subject to breaking tension in the Instron tester as referred to in Example 2. Results were as follows:

| Composition | Control | Illustrative | |
|---|---|---|---|
| | 5 | 8th | 9th |
| Amount of itaconic anhydride (% by weight of composition) | 0 | 0.5 | 1.5 |
| Tensile shear strength (Kp/cm²) | 40 | 59 | 91 |

These results show that when bonds are formed, a greater tensile shear strength is achieved after 2 minutes cure with compositions including quantities of itaconic acid anhydride, and that greater tensile shear strengths are obtainable with the larger amount of itaconic acid anhydride.

EXAMPLE 6

This example shows improved heat resistance of adhesive bonds formed by use of allyl-2-cyanoacrylate adhesive including itaconic acid anhydride.

One drop of Control composition 6, which comprised allyl-2-cyanoacrylate stabilized as in Control Composition 1, was placed between two brass sheets (dimensions 150 × 10 × 5 mm) which had been thoroughly cleaned with acetone. The bonded sheets were warmed to 100°C. for 24 hours. After cooling to room temperature a tensile shear strength of 34 Kp/cm² was obtained using an Instron tester as referred to in Example 2.

A 10th illustrative composition was made from a sample of Control composition 6 by addition of an amount of itaconic acid anhydride to provide 1% by weight of the tenth illustrative composition. The tensile shear strength of a brass-brass bond formed (in the same way as with Control composition 6 using this 10th illustrative composition and aged at 100°C. for 24 hours was measured as just above referred to and found to be 135 Kp/cm².

EXAMPLE 7

The tensile shear strength of adhesive bonds made using the first and third illustrative compositions (see Examples 1 and 4) was measured in relation to the cure time. The bonds were made, aged at room temperature, and tested as in Example 2 except that the time (cure time) between making the bonds and testing them on the Instron machine was varied.

The results indicate a progressive increase in bond strength, and it is noted that after 15 minutes, the tensile shear strength result for the third illustrative composition is in excess of the value for Control composition 3 after ageing for 1 hour, and the tensile shear strength results for both the first and second illustrative compositions after 1 hour cure time is well in excess of results obtained with control compositions 1 and 3 as shown by Examples 2 and 4.

Having thus described my invention, what I claim as new and desire to secure as Letters Patent of the United States is as follows:

1. An adhesive composition comprising one or more polymerizable esters of 2-cyanoacrylic acid according to the general formula

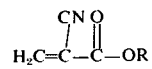

where R is an alkyl or alkenyl group having 1 to 16 carbon atoms, a cyclohexyl group or a phenyl group, together with an anionic polymerization inhibitor and a free radical polymerization inhibitor, characterized in that the adhesive includes from about 0.1 to about 10% by weight based on the weight of the composition of a compound according to the formula

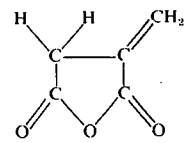

2. An adhesive composition according to claim 1 wherein the ester of 2-cyanoacrylic acid includes at least one member of the group consisting of methyl-2-cyanoacrylate, ethyl-2-cyanoacrylate and allyl-2-cyanoacrylate said composition containing from about 0.5% to about 3.0% 0% by weight based on the weight of the composition of itaconic acid anhydride, said free radical polymerization inhibitor being selected from the group consisting of hydroquinone and the monomethyl ether of hydroquinone and said anionic polymerization inhibitor being selected from the group consisting of $P_2O_5$ and $SO_2$.

3. An adhesive composition according to claim 2 wherein the ester of 2-cyanoacrylic acid is a mixture of methyl-2-cyanoacrylate and up to about 50% by weight of the mixture of ethyl-2-cyanoacrylate or allyl-2-cyanoacrylate.

4. An adhesive composition according to claim 3 comprising a mixture of about 98% by weight methyl-2-cyanoacrylate and about 2% by weight allyl 2-cyanoacrylate.

5. An adhesive composition according to claim 2 comprising from about 0.01 to about 0.02% by weight of the composition of said free radical polymerization inhibitor and about 0.001% by weight of the composition of said anionic polymerization inhibitor.

\* \* \* \* \*

| Cure Time | 2 Min. | 15 Min. | 1 Hr. | 24 Hrs. |
|---|---|---|---|---|
| First illustrative composition Tensile shear strength (Kp/cm²) | 95 | 153 | 182 | 223 |
| Third illustrative composition Tensile shear strength (Kp/cm²) | 103 | 161 | 200 | 242 |